(12) United States Patent
Powers

(10) Patent No.: US 6,234,967 B1
(45) Date of Patent: May 22, 2001

(54) ULTRASONIC DIAGNOSTIC IMAGING SYSTEMS WITH POWER MODULATION FOR CONTRAST AND HARMONIC IMAGING

(75) Inventor: Jeffry E. Powers, Bainbridge Is., WA (US)

(73) Assignee: ATL Ultrasound, Bothell, WA (US)

( * ) Notice: Subject to any disclaimer, the term of this patent is extended or adjusted under 35 U.S.C. 154(b) by 0 days.

(21) Appl. No.: 09/216,693

(22) Filed: Dec. 18, 1998

(51) Int. Cl.$^7$ .................................................. A61B 8/00
(52) U.S. Cl. ................................. 600/443; 600/458
(58) Field of Search .......................... 600/443, 440–442, 600/447, 437, 458

(56) References Cited

U.S. PATENT DOCUMENTS

| | | | |
|---|---|---|---|
| 5,301,168 | * 4/1994 | Miller | 367/138 |
| 5,456,257 | 10/1995 | Johnson et al. . | |
| 5,482,046 | * 1/1996 | Deitrich | 600/458 |
| 5,560,364 | 10/1996 | Porter . | |
| 5,617,862 | * 4/1997 | Cole et al. | 600/447 |
| 5,640,959 | * 6/1997 | Hara et al. | 600/447 |
| 5,685,310 | 11/1997 | Porter . | |
| 5,694,937 | * 12/1997 | Kamiyama | 600/458 |
| 5,740,128 | 4/1998 | Hossack et al. . | |
| 5,833,613 | 11/1998 | Averkiou et al. . | |
| 5,833,615 | * 11/1998 | Wu et al. | 600/458 |
| 5,860,931 | * 1/1999 | Chandler | 600/458 |
| 5,873,830 | * 2/1999 | Hossack et al. | 600/447 |
| 6,045,506 | * 4/2000 | Hossack | 600/443 |

FOREIGN PATENT DOCUMENTS 0 770 352   5/1997   (EP) .

* cited by examiner

Primary Examiner—Francis J. Jaworski
(74) Attorney, Agent, or Firm—W. Brinton Yorks, Jr.

(57) ABSTRACT

A method and ultrasonic diagnostic imaging system for contrast agent imaging or tissue harmonic imaging is described which modulates the transmit power as a function of the angle of an electronically steered beam or the location of the beam in the scan plane to compensate for the reduction in delivered energy to points in the image field resulting from off-angle steering or a reduction in the number of elements of the transmit aperture.

27 Claims, 1 Drawing Sheet

ULTRASONIC DIAGNOSTIC IMAGING SYSTEMS WITH POWER MODULATION FOR CONTRAST AND HARMONIC IMAGING

This invention relates to ultrasonic diagnostic imaging systems and, in particular, to beam transmission for ultrasonic harmonic diagnostic imaging.

U.S. Pat. Nos. 5,833,613 and 5,456,257, of which I am a co-inventor, describe techniques for ultrasonic imaging with contrast agents at both fundamental and harmonic frequencies. The former patent describes harmonic imaging techniques whereby microbubble contrast agents are insonified with acoustic energy of intensities sufficient to cause the microbubbles to oscillate nonlinearly and thereby return echo signals containing harmonic signal components. The latter patent describes a contrast technique whereby microbubble contrast agents are insonified with an even greater intensity of acoustic energy, causing the microbubbles to become disrupted. The disruption of the microbubbles also causes the microbubbles to return echo signals containing harmonic signal components. In practice however the microbubble effects which develop these nonlinear signal components are not always easy to produce in a uniform manner over the image field. The present invention is directed to the more efficient, uniform development and control of these effects, as well as tissue harmonic imaging effects.

In accordance with the principles of the present invention, the power level of transmit waves used to image contrast agents is varied with changes in the transmit beam aperture. In one embodiment these changes comprise changes in the angle of incidence between the transmit beam and the plane of the transmitting array transducer, as occurs in phase array (sector) scanning. In another embodiment these changes comprise changes in the transmit aperture size, as occur at the extremes of a linear scanning array transducer. The same principles are used in tissue harmonic imaging to develop a uniform level of harmonic signal development across the image field.

There are three modes of use of ultrasonic microbubble contrast agents. One is to transmit ultrasonic energy to the microbubbles, which reflect some of the energy back to the transmitting transducer in the form of an echo at the transmit frequency. This mode of contrast agent use relies upon the sharp impedance mismatch at the gas-tissue (or gas-blood) interface of the microbubbles to strongly reflect echoes from the transmitted wave energy. This mode is substantially the same as standard pulse-echo imaging, but with improved signal to noise performance due to the impedance mismatch.

A second mode of use is to transmit energy which is sufficient to cause the microbubbles to oscillate nonlinearly, which returns echoes containing both fundamental and harmonic frequency components. This mode permits effective segmentation of the contrast agent by the ultrasound receiver/detector, because the harmonic signals can be separated from fundamental echo components and imaged. While filters can be used to separate the harmonic frequencies, the preferred technique for such separation is called pulse inversion imaging.

A third mode of use of contrast agents is to transmit sufficient energy to disrupt the microbubbles, causing them to break up, burst, or dissolve rapidly. These effects are sharply nonlinear, returning strong and harmonic signal components.

The present invention is premised upon the hypothesis that the nonlinear oscillation of microbubbles and the disruption of microbubbles are threshold effects, that is, a threshold level of energy is required to cause each effect. Accordingly, to cause the desired effect at every location where a contrast agent is present in the image, it is necessary to deliver energy at or above the appropriate threshold for the desired effect to every microbubble in the image. The important factor is not the transmit energy applied to the transducer, but the energy which ultimately reaches the microbubbles. This energy is affected by a number of factors, such as absorption and scattering of ultrasonic energy by the tissue through which the transmitted energy passes on its path to the contrast agent. A second factor, which is addressed by the present invention, is changes in the transmit aperture of the transducer.

Figure 1:
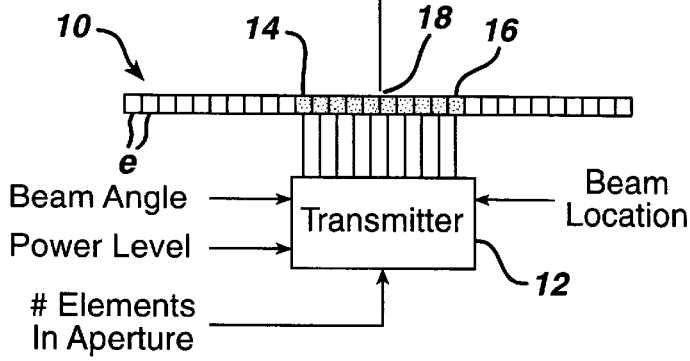
FIG. 1 illustrates a transmitting transducer array from which a beam normal to the array is transmitted.

Referring first to FIG. 1, a transmitter 12 is coupled to a plurality of elements e of a transducer array 12 which are shaded in the drawing. These shaded elements comprise the transmit aperture of the array in this example. When the transmitter 12 sequentially excites the shaded elements beginning with the most outward elements 14, 16 and progressively exciting more inward elements toward the center 18 of the transmit aperture, an ultrasonic beam is transmitted normal to the face of the transducer array as shown by beam 20. When the transmitted beam is at or above the appropriate threshold, the energy delivered to a microbubble 22 in the image plane can be sufficient to cause the microbubble to oscillate nonlinearly or become disrupted, thereby returning a significant nonlinear (harmonic) echo signal.

Figure 2:
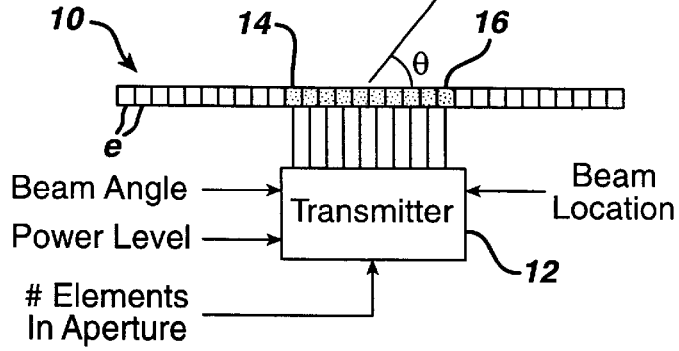
FIG. 2 illustrates a transmitting transducer array from which a beam at an acute angle of incidence to the array is transmitted.

The beam 20 may also be steered at an acute angle θ to the face of the transducer array 10 during sector or phased array scanning as shown in FIG. 2. To steer the beam 20 in the illustrated direction the array elements are progressively excited from element 14 at the left to element 16 at the right. Customarily a sequential element excitation pattern for beam focusing is combined with the beam steering excitation pattern. However, when the transducer elements in FIG. 2 are excited with the same transmit energy from the transmitter 12 as they were in FIG. 1, the off-axis steering of the beam 20 (that is, off of the straight ahead direction of the beam of FIG. 1) will result in reception of a lower level of energy at microbubble 24 than was the case with microbubble 22 at the same beam distance. This means that microbubbles directly in front of the center of the array will be caused to exhibit the desired nonlinear effect at deeper depths than is the case with microbubbles located at the lateral sides of the array.

In accordance with the principles of the present invention, the transmitter 12 applies more power to the transducer elements e when transmitting in off-axis directions than when transmitting normal to the transducer. This will cause a greater uniformity in the inducement of the desired nonlinear effect across the image field. If it is desired to cause the nonlinear effect everywhere in the image, this modulation of transmit power as a function of beam angle can cause the threshold necessary for the desired effect to be met everywhere in the image, rather than predominately at the center. In a preferred embodiment, as the angle θ declines as the beam is steered to the lateral sides of the sector, the transmit power (e.g., voltage) applied to the transmit aperture elements is progressively increased as a function of 1/sin θ, to compensate for the rate at which the transmit power falls off.

Figure 3:
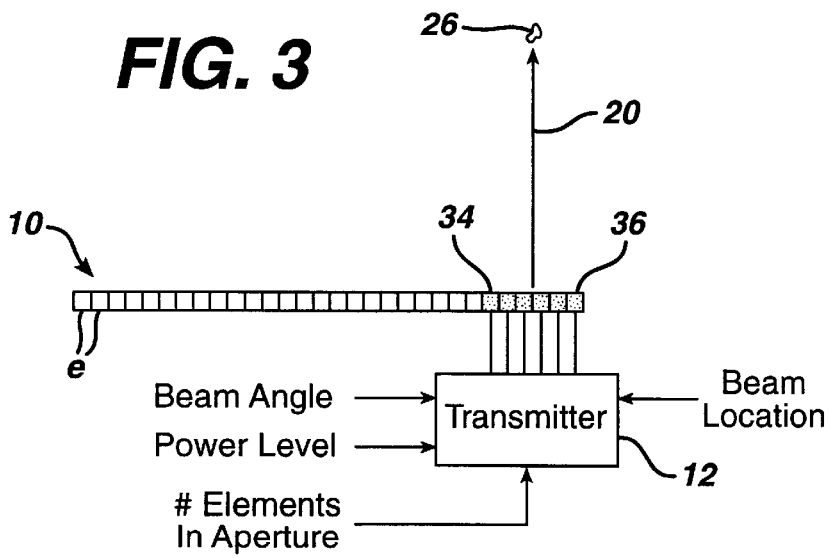
FIG. 3 illustrates a transmitting transducer array from which a beam is transmitted near an end of the array.

Another manifestation of the problem of nonuniform microbubble excitation is shown in FIG. 3. In this drawing the transducer array 10 is operated as a linear array, with a transmit subaperture shifted across the array to transmit beams in parallel from the array but emanating from different points across the array. The parallel beams may all be steered normal to the face of the array, or all may be steered at a common angle to the face of the array. As the transmit subaperture reaches an end of the array, there are no longer elements available to add to the shifting subaperture as there were when the subaperture was shifted at the center of the array. With fewer elements 34–36 in the lateral subapertures, the transmitted energy which reaches microbubble 26 will be less than in the case of transmission with a fully sized subaperture at the array center. In accordance with the present invention, when the number of elements of the transmit subaperture begins to decline, the transmit power applied to the transducer elements is increased to maintain uniformity in the energy level which reaches points in the image field across the image field. Thus, microbubbles at the lateral sides of the image will experience the same threshold phenomena as microbubbles in the center of the image at the same depth of field.

The same principle can be applied to tissue harmonic imaging and used to maintain a uniform signal to noise ratio across the image rather than experience a falloff of the signal to noise ratio at the lateral extremes of the image. The harmonic components used in tissue harmonic imaging are not transmitted by the transducer but develop with increasing distortion of the transmitted wave as it progresses through the tissue. To maintain signal to noise uniformity across the image, the power applied to the elements of the transmit aperture is increased as the electronically steered beam angle θ is decreased during sector scanning. When tissue harmonic imaging is performed by linear scanning, the power applied to the elements of the transducer is increased as the number of elements of the transmit aperture decreases. In a preferred linear array scanning embodiment, the total amount of power applied to the elements of the transmit aperture is maintained constant for as long as is reasonably possible as the transmit aperture approaches a lateral extreme of the image field.

Other variations of the application of the principles of the present invention will be apparent to those skilled in the art. For instance, the transmit power can be maintained constant for beams departing only a small amount from normal, then increased when the transmit beam angle declines to a predetermined angle. The embodiment of FIG. 3 is useful for both planar linear and curved array scanning. Lateral transmit power variation is also useful in cardiac imaging to improve the image uniformity of walls of the heart chamber which are substantially parallel to the beam direction. Lateral transmit power variation is helpful to improve the uniformity of phase array imaging, independent of contrast or harmonic mode imaging.

What is claimed is:

1. A method for ultrasonic diagnostic imaging of contrast agents with an array of transducer elements having a face surface opposing a target region and exhibiting a transmit aperture comprising the steps of:
   applying a given level of transmit power to the elements of the transmit aperture when a beam is transmitted normal to the face surface of the array so as develop a desired mode of microbubble behavior at a target region at a given depth; and
   applying a level of transmit power to the elements of the transmit aperture which is in excess of said given level when a beam is transmitted at an off-angle to the face surface of the array so as to develop substantially the same mode of microbubble behavior at a target region of equivalent depth.

2. The method of claim 1, wherein said transmit power is controlled so that said beams act to develop substantially the same ultrasonic harmonic effect at substantially uniform depths across an ultrasonic image.

3. The method of claim 2, wherein said desired ultrasonic harmonic effect comprises nonlinear oscillation of a microbubble.

4. The method of claim 2, wherein said desired ultrasonic harmonic effect comprises disruption of a microbubble.

5. The method of claim 1, wherein said transmit power is controlled so that said beams act to develop a desired ultrasonic harmonic effect at all depths of an ultrasonic image.

6. The method of claim 5, wherein said desired ultrasonic harmonic effect comprises nonlinear oscillation of a microbubble.

7. The method of claim 5, wherein said desired ultrasonic harmonic effect comprises disruption of a microbubble.

8. A method for ultrasonic diagnostic imaging of contrast agents with an array of transducer elements having a face surface opposing a target region and exhibiting a transmit aperture comprising the steps of:
   applying a given level of transmit power to the elements of the transmit aperture when a beam is transmitted normal to the face surface of the array; and
   applying progressively increasing levels of transmit power to the elements of the transmit aperture as beams are transmitted at increasingly acute angles to the face surface of the array.

9. The method of claim 8, wherein said transmit power is controlled so that said beams act to develop substantially the same ultrasonic harmonic effect at substantially uniform depths across an ultrasonic image.

10. The method of claim 9, wherein said desired ultrasonic harmonic effect comprises nonlinear oscillation of a microbubble.

11. The method of claim 9, wherein said desired ultrasonic harmonic effect comprises disruption of a microbubble.

12. The method of claim 8, wherein said transmit power is controlled so that said beams act to develop a desired ultrasonic harmonic effect at all depths of an ultrasonic image.

13. The method of claim 12, wherein said desired ultrasonic harmonic effect comprises nonlinear oscillation of a microbubble.

14. The method of claim 12, wherein said desired ultrasonic harmonic effect comprises disruption of a microbubble.

15. A method for using an array of ultrasonic transducer elements having a face surface opposing a target region and exhibiting a transmit aperture to perform tissue harmonic imaging comprising the steps of:
   applying a given level of transmit power to the elements of the transmit aperture when a beam is transmitted normal to the face surface of the array so as develop a desired harmonic effect at a target region at a given depth; and
   applying a level of transmit power to the elements of the transmit aperture which is in excess of said given level when a beam is transmitted at an off-angle to the face surface of the array so as to develop substantially the same harmonic effect at a target region of equivalent depth.

16. The method of claim 15, wherein the second step comprises applying progressively increasing levels of transmit power to the elements of the transmit aperture as beams are transmitted at increasingly acute angles to the face of the array.

17. The method of claim 15, wherein said transmit power is controlled so that said beams act to develop substantially the same level of harmonic signal content at substantially uniform depths across an ultrasonic image.

18. An ultrasonic diagnostic imaging system for imaging with contrast agents comprising:

an array transducer including a plurality of transducer elements; and a transmitter coupled to individual elements of said array transducer which is adapted to apply levels of transmit power to said elements which vary as a function of the location of the transmit beam in the image plane so as to produce a more uniform harmonic effect at points in an image field of equivalent depth.

19. The ultrasonic diagnostic imaging system of claim 18, wherein said levels of transmit power applied by said transmitter are controlled to vary as a function of the lateral location of the transmit beam.

20. The ultrasonic diagnostic imaging system of claim 18, wherein said levels of transmit power applied by said transmitter are increased by said transmitter as the angle of the transmit beam to the face of the array transducer declines.

21. The ultrasonic diagnostic imaging system of claim 18, wherein said transmitter transmits a sector beam pattern, and wherein the level of transmit power applied to transmit a beam at the center of the sector is less than the level of transmit power applied to transmit a lateral beam of the sector.

22. The ultrasonic diagnostic imaging system of claim 18, wherein said transmitter acts to transmit a parallel beam pattern, and wherein the level of transmit power applied by said transmitter to transmit a beam varies as a function of the number of transducer elements of an active transmit aperture.

23. The ultrasonic diagnostic imaging system of claim 18, wherein said array transducer performs linear array scanning by using different active transmit apertures for different beams, and wherein said transmitter acts to apply increased levels of transmit power to said elements as the active transmit aperture approaches a lateral extreme of the array.

24. An ultrasonic diagnostic imaging system for performing tissue harmonic imaging comprising:

an array transducer including a plurality of transducer elements; and a transmitter coupled to individual elements of said array transducer which applies levels of transmit power to said elements which vary as a function of the location of the transmit beam in the image plane so as to produce a more uniform harmonic effect at points in an image field of equivalent depth.

25. The ultrasonic diagnostic imaging system of claim 24, wherein said levels of transmit power are increased by said transmitter as the angle of the transmit beam to the face of the array transducer declines.

26. The ultrasonic diagnostic imaging system of claim 24, wherein said transmitter transmits a sector beam pattern, and wherein the level of transmit power used for a beam at the center of the sector is less than the level of transmit power used for a lateral beam of the sector.

27. An ultrasonic diagnostic imaging system for performing tissue harmonic imaging comprising:

an array transducer including a plurality of transducer elements which are used to form a plurality of active transmit apertures; and a transmitter coupled to individual elements of said array transducer which applies levels of transmit power to said elements which vary as a function of the number of elements in the active transmit aperture so as to produce a more uniform harmonic effect at points in an image field of equivalent depth.

* * * * *